(12) United States Patent
Kobayashi

(10) Patent No.: US 6,525,227 B1
(45) Date of Patent: Feb. 25, 2003

(54) METHOD OF REACTION IN WATER CATALYZED BY LEWIS ACID

(75) Inventor: Shu Kobayashi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/762,102

(22) PCT Filed: Aug. 4, 1999

(86) PCT No.: PCT/JP99/04200

§ 371 (c)(1),
(2), (4) Date: Apr. 4, 2001

(87) PCT Pub. No.: WO00/07719

PCT Pub. Date: Feb. 17, 2000

(30) Foreign Application Priority Data

Aug. 4, 1998  (JP) ........................... 10-220915

(51) Int. Cl.$^7$ ......................... C07C 45/00; C07C 49/04; C07C 47/02
(52) U.S. Cl. ...................... 568/388; 568/414; 568/463; 568/496
(58) Field of Search ................ 568/388, 414, 568/463, 496

(56) References Cited

FOREIGN PATENT DOCUMENTS

| JP | 9-248463 | 9/1997 |
|---|---|---|
| JP | 9-262479 | 10/1997 |
| JP | 9-290163 | 11/1997 |
| JP | 10-24234 | 1/1998 |
| JP | 11-180900 | 7/1999 |

OTHER PUBLICATIONS

Merck Index, 11th edition, p. 414, #2651 (1983).*
Kobayashi et al, Tetrahedron Letters, vol. 38, pp. 4559–4562 (1997).*

* cited by examiner

*Primary Examiner*—Johann Richter
*Assistant Examiner*—Sikarl A. Witherspoon
(74) *Attorney, Agent, or Firm*—Wenderoth, Lind & Ponack, L.L.P.

(57) ABSTRACT

A reaction method by a novel Lewis acid catalyst stable in water for organic synthesis by using a metal compound stable in water and functioning as a Lewis acid catalyst and using water as apart or all of a solvent, the metal ion of the metal compound having a hydrolysis constant (pKh) of: $4.3 \leq pKh \leq 10.1$ and a water exchange rate constant (WERC) of $3.2 \times 10^6 M^{-1} sec^{-1}$ or more.

4 Claims, 1 Drawing Sheet

Fig. 1

METHOD OF REACTION IN WATER CATALYZED BY LEWIS ACID

This application is a 371 of PCT/JP99/04200 filed Aug. 4, 1999.

BACKGROUND OF THE INVENTION

1. Field of the Invention

This invention concerns a method of reaction in water catalyzed by Lewis acid. More specifically, this invention relates to a novel method of reaction in water catalyzed by Lewis acid, which carries out organic synthesis reactions using Lewis acid that constitute kerners of not only organic synthesis chemistry but also modern fine organic chemistry such as polymer chemistry and material chemistry, by using water as a part or all of the solvent and under the presence of a Lewis acid which is stable in water.

2. Description of the Related Art

Various organic chemical reactions using general Lewis acids such as $AlCl_3$ or finely designed Lewis acids such as $HF—BF_3$ as the catalyst have been known in experimental method or industrial method (Chemistry and Industry, vol. 50, No. 10 (1997) 1481–1501). Then, organic synthesis for high addition value chemical products such as novel advanced functional compounds, fine chemical products, polymeric compounds for medicinal and agricultural chemicals has become more and more important in recent years, and Lewis acid catalysts have been used generally for the organic synthesis reactions, exhibited their performance in various fields and have been used generally as indispensable catalysts.

On the other hand, development for chemical reactions or processes considering human or global environments has recently been demanded socially, and regulations for organic solvents such as benzene or halogen-containing solvents have become severer year by year, so that synthesis technology of conducting various organic reactions in aqueous solvents has been highlighted and requirement has been increased also in the organic synthesis reactions using the Lewis acid as the catalyst.

However, metal ions from metal compounds used as the Lewis acid mainly include those ions from group IB, group IIB, group IIIB, group IVA, group IVB and group III belonging to the periodical table and, for example, $AlCl_3$ or $BF_3$ from the IIIB group metal as the typical Lewis acid is rapidly hydrolyzed. Further, most of Lewis acids of the metals in each group are rapidly reacted with water and hydrolyzed to be inactivated, so that it has been considered so far that use of the Lewis acid in an aqueous solution is impossible.

However, the inventor of the present application has recently found that rare earth metal trifluoro methane sulfonates (rare earth triflate) are stable also in water and function as the Lewis acid in the aqueous solution (Journal of the Society of Organic Synthesis Chemistry, 53, 370 (1995)). Since the rare earth triflates are dissolved more easily in water than in organic solvents, they can be recovered easily by extraction after the completion of the reaction and the catalytic activity is not lost even by repeated use of several times. However, for such novel finding made by the inventor of the present application, no sufficient study has yet been made as to whether they show appropriate Lewis acid catalytic activity under the reaction conditions in the aqueous system usable industrially or as to whether the reactions can be carried out at a high yield in the aqueous system with regard to the entire Lewis acid, so that an appropriate Lewis acid catalyst has been selected by trial and error. Accordingly, it has been desired to establish general rules or indications for enabling rapid selection therefor.

If the metal compounds including the rare earth triflates described above which are stable also in water and function as the Lewis acid can be defined clearly along the general rules or indications, it will be possible to design a generally applicable, environment-preserving type organic synthesis systems basically free from the requirement for discarding of the catalyst and to expect attainment of organic chemical reactions which use an aqueous solution and which are so to speak gentle to environment. Accordingly, establishment of more comprehensive and generally applicable technology for reactions in water catalyzed by Lewis acid has been an extremely important subject.

This invention of the present application has been achieved in view of the foregoing situations and it is an object thereof to provide a more comprehensive and generally applicable novel method of reaction in water catalyzed by Lewis acid, basically free from the requirement for discarding the catalyst and employing water as a part or all of the solvent, which is gentle to global environments and safe to social environments including human beings.

DISCLOSURE OF THE INVENTION

For solving the subject described above, the invention of the present application provides, at first, a method of reaction in water catalyzed by a Lewis acid for an organic synthesis reaction method by using a metal compound stable in water and functioning as a Lewis acid and employing water as a part or all of a solvent, wherein the hydrolysis constant (pKh) of the metal ion of the metal compound is within a range: $4.3 \leq pKh \leq 10.1$ and the water exchange rate constant (WERC) thereof is $3.2 \times 10^6 M^{-1} sec^{-1}$ or more, and wherein the metal ion of the metal compound is iron (II) ion, copper (II) ion or lead (II) ion.

BRIEF DESCRIPTION OF THE DRAWING

FIG. 1 is a view showing the periodical table in which metal ion portions are taken out for showing the hydrolysis constant and the water exchange rate constant when each of the metals is ionized. The portion surrounded with a fat solid line shows metal ion species of the metal compound and physical property constant as the aqueous system Lewis acid catalyst according to this invention.

DESCRIPTION OF THE PREFERRED EMBODIMENT

This invention having the foregoing feature is to be explained with reference to preferred embodiments.

At first, in the aqueous system Lewis acid catalyst of this invention, it is essential for the metal compound which is stable in water and functions as a Lewis acid that the hydrolysis constant (pKh) of the metal ion constituting the metal compound is within a range: $4.3 \leq pKh \leq 10.1$. The hydrolysis constant (pKh) is determined by the following equations (Baes, Jr. C. F.: Mesmer, R. The Hydrolysis of Cations Willy: New York, 1976).

$$pKn = -|log K_{xy}$$

$$K_{xy} = \frac{[M_x(OH)_y^{(xz-y)+}][N^+]^y}{[M^{z+}]^x} \cdot \frac{g_{xy} g_{H+}^y}{g_{MZ+}^x a_{H2O}^y}$$

$$xM^{z+} + yH_2O \rightleftharpoons M_x(OH)_y^{(xz-y)+} + yH^+$$

The metal compound Lewis acid with the pKh value of less than 4.3 is hydrolyzed to form oxonium ions. On the other hand, when the pKh value is more than 10.1, the neutralization energy for the metal ion is decreased to lower the Lewis acidity.

Accordingly, the hydrolysis constant (pKh) should be within the range described above.

Further, in this invention, the water exchange rate constant (WERC) of the Lewis acid metal compound is $3.2 \times 10^6 M^{-1} sec^{-1}$ or more. The water exchange rate constant (WERC) is measured by a nuclear magnetic resonance absorption, acoustic wave absorption or polyligand method (Martell, A. B. Ed. Coordination Chemistry, Vol. 2, ACS Monograph 168, ACS: Washington, D.C., 1978).

When the WERC value is $3.2 \times 10^5 M^{-1} sec^{-1}$ or less, the catalytic activity is lowered to scarcely obtain an aimed product. This is because the Lewis acidity is lowered in view of the relation with the hydration energy of the metal ion when the WERC value is small.

Figure 1:
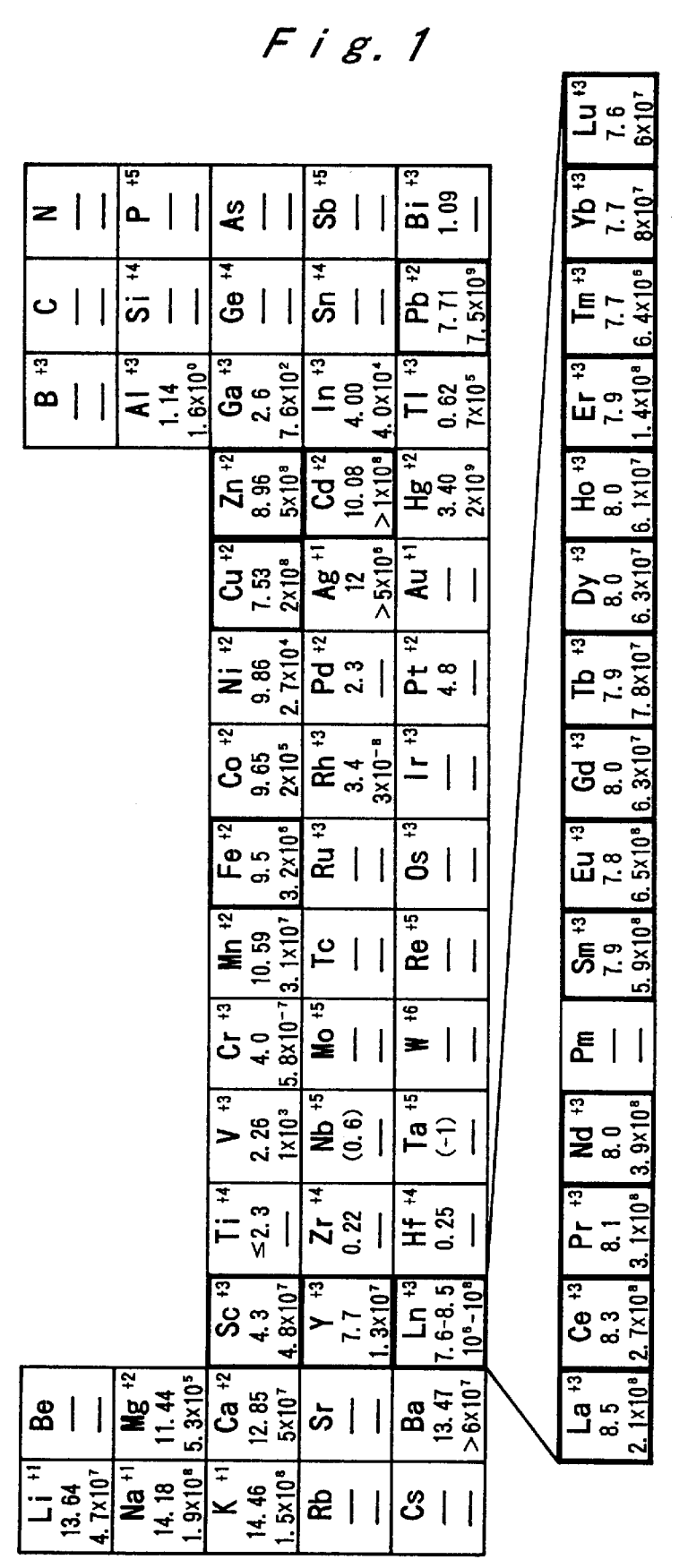

FIG. 1 shows the hydrolysis constant and the water exchange rate constant determined when metal ions are formed.

In FIG. 1, there are exemplified copper (II) ions as the IB group metal, zinc (II) ion and cadmium (II) ion as the IIB group metal, and lead (II) ion as the VI group metal, and iron (II) ion is exemplified as the VIII group metal. In this invention, the metal compound to be used as the Lewis acid, halides, perhalogenate compounds and trifluroalkane sulfonates of the metals described above can be used and, perchlorate compounds and trifluoromethane sulfonates are preferably used. In the case of zinc (II) ion and cadmium (II) ion, they are used as perhalogenates and trifluoroalkane sulfonates.

For example, in the method of this invention using the metal compounds described above as the aqueous system Lewis acid catalyst, the amount of the metal compound used based on the reaction material substrate is properly selected depending on the kind of the organic synthesis reaction. Generally, the molar ratio to the raw material substrate can be approximate as a range from 0.001 to 1.

Further, the surfactant may be used for the reaction. As the surfactant to be used, soap, alkylbenzene sulfonate and sodium dodecylsulfonate can be used as an anionic surfactant, and polyoxyethylene alkyl ether, polyoxyethylene alkyl phenolate, sorbitan fatty acid ester and sucrose fatty acid ester can be used as a noionic surfactant. Preferably, sodium dodecyl sulfate and triton X-100 are used.

When the surfactant is used, it is considered that the amount of use ranges from 0.001 to 10 times the amount of the metal compound described above. The surfactant can be used depending on the case where water is used as a portion of a solvent to form a mixed system with an organic solvent or depending on the degree of hydrophilic or hydrophobic property of the reaction material substrate.

In the reaction method of this invention, water is used as a part or all of the solvent. The amount of water or water with the organic solvent used as the solvent, the reaction temperature or reaction pressure and, further, the reaction time are properly determined depending on the kind of the organic synthesis reaction to which the method of the invention is applied.

There is no particular restriction on the reactions to which the Lewis acid of this method of reaction in water catalyzed by the invention is applicable, but those shown below can be mentioned, for example.

β-aminoketone and β-aminoester can be prepared by carrying out Mannich reaction, homoallyl alcohol or homoallyl amine can be produced by carrying out a direct allylating reaction, and β-hydroxyketone and β-hydroxyester can be prepared by carrying out aldol reaction. Further, alkylation reaction and polymerization reaction as the Lewis acid catalyzed reaction are also the object of this invention.

EXAMPLE

Then, the method of this invention is further explained more concretely. This invention is not of course restricted to such examples unless they do not go beyond the gist thereof.

Example 1

In accordance with the following reaction scheme:

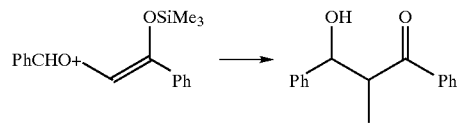

0.1 mol of benzaldehyde and 0.1 mol of 1-phenyl-1-trimethylsiloxypropene were dissolved in a mixed solvent of water and tetrahydrofuran (THF) (1:9), to which 0.2 equivalent amount of the compound in Table 1 was added and then stirred at a room temperature for 12 hours. After distilling off the solvent, the aldol condensates were obtained at the yield as shown below.

TABLE 1

| Metal compound Lewis acid | Aldol condensate yield (%) |
|---|---|
| FeCl$_2$ | 39 |
| Cu(ClO$_4$)$_2$ | 47 |
| Zn(ClO$_4$)$_2$ | 46 |
| Cd(ClO$_4$)$_2$ | 49 |

Example 2

The aldol condensation reaction in Example 1 was carried out using a mixed solvent of water:ethanol:toluene (1:7:3). The metal compound Lewis acids and the reaction yields of the aldol condensates are shown below.

TABLE 2

| Metal compound Lewis acid | Aldol condensate yield (%) |
|---|---|
| Fe(ClO$_4$)$_2$ | 55 |
| Cd(ClO$_4$)$_2$ | 81 |
| Cd(ClO$_4$)$_2$ | 72 |
| Pb(ClO$_4$)$_2$ | 65 |

Comparative Example

The aldol condensation reaction of Example 1 was further carried out using other metal compounds. As a result, when each of LiCl, NaCl, MgCl$_2$, PCl$_3$, KCl, CaCl$_2$, GeCl$_2$, $RuCl_3$, $SbCl_3$, $BaCl_2$, and $OsC_2$ was used, no aldol condensate was formed but the starting reaction material compound was recovered. Further, when each of $BCl_3$, $SiCl_4$, $PCl_5$, $TiCl_4$, $VCl_3$, $ZrCl_4$, $NbCl_5$, $MoCl_5$, $SnCl_4$, $SbCl_5$, $HfCl_4$, $TaCl_5$, $WCl_6$, $ReCl_5$, and $TiCl_3$ was used, no aldol condensate was formed but the silyl enol ether of the starting compound was decomposed.

Further, even in a case where formation of the aldol condensates was scarcely recognized, only the following results were obtained.

TABLE 3

| Metal compound | Aldol condensate yield (%) |
|---|---|
| $MnCl_2$ | trace |
| $CrCl_2$ | trace |
| $CoCl_2$ | trace |
| $NiCl_2$ | trace |
| $AgCl$ | trace |
| $SnCl_2$ | 4 |
| $RhCl_3$ | trace |
| $AlCl_3$ | trace |
| $GaCl_3$ | trace |
| $PdCl_2$ | trace |
| $PtCl_2$ | trace |
| $HgCl_2$ | trace |
| $BiCl_3$ | trace |

As has been described above specifically, this invention provides a novel Lewis acid catalyst stable in water and an organic synthesis reaction method using the same. According to the method of this invention, use of organic solvents can be decreased and the reaction can be carried out without using them at all. Then, since the catalytic activity of the Lewis acid is maintained, it is possible to design a system capable of recovering and reusing the catalyst to 100%, and it is also possible to attain fine in vivo reactions in a more simple from reaction by using metal chelation instead of hydrogen bonds in a flask as the reaction in water catalyzed by the Lewis acid.

What is claimed is:

1. A method of conducting a Mannich reaction, an allylation reaction, or an aldol reaction in water catalyzed by a Lewis acid, which consists of conducting the reaction using a metal compound stable in water and functioning as a Lewis acid and employing water as a part or all of a solvent, wherein the hydrolysis constant (pKh) of a metal ion of the metal compound is within a range: $4.3 \leq pKh \leq 10.1$ and the water exchange rate constant (WERC) thereof is $3.2 \times 10^6 M^1 sec^{-1}$ or more, and wherein the metal ion is iron (II) ion, copper (II) ion, or lead (II) ion.

2. The method as defined in claim 1, wherein the metal compound is a trifluoromethane sulfonate or perchlorate of the metal ion.

3. A method of conducting a Mannich reaction, an allylation reaction or an aldol reaction in water catalyzed by a Lewis acid, which consists of conducting the reaction using a metal compound stable in water and functioning as a Lewis acid and employing water as a part or all of a solvent, wherein the metal compound includes a metal ion which is iron (II) ion, copper (II) ion, or lead (II) ion.

4. A method of identifying an aqueous system Lewis acid catalyst, which consists of testing metal compounds, and identifying a metal compound which is stable in water and functions as a Lewis acid, wherein the hydrolysis constant (pKh) of a metal ion of the metal compound is within a range: $4.3 \leq pKh \leq 10.1$ and the water exchange rate constant (WERC) thereof is $3.2 \times 10^6 M^{-1} sec^{-1}$ or more.

* * * * *